(12) United States Patent
Hopkins et al.

(10) Patent No.: US 10,687,949 B2
(45) Date of Patent: *Jun. 23, 2020

(54) SHOULDER PROSTHESIS AND COMPONENTS THEREOF

(71) Applicant: ZIMMER GMBH, Winterthur (CH)

(72) Inventors: Andrew Hopkins, Winterthur (CH); Philippe Hardy, Paris (FR)

(73) Assignee: ZIMMER GMBH, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/684,578

(22) Filed: Aug. 23, 2017

(65) Prior Publication Data

US 2017/0348111 A1 Dec. 7, 2017

Related U.S. Application Data

(63) Continuation of application No. 14/439,605, filed as application No. PCT/EP2013/077419 on Dec. 19, 2013, now Pat. No. 9,763,797.

(30) Foreign Application Priority Data

Dec. 27, 2012 (EP) .................................... 12199430

(51) Int. Cl.
*A61F 2/40* (2006.01)
*A61F 2/30* (2006.01)

(52) U.S. Cl.
CPC .............. *A61F 2/40* (2013.01); *A61F 2/4014* (2013.01); *A61F 2/4081* (2013.01);
(Continued)

(58) Field of Classification Search
CPC ........ A61F 2/40; A61F 2/4081; A61F 2/4014; A61F 2002/4018
See application file for complete search history.

(56) References Cited

U.S. PATENT DOCUMENTS 4,003,095 A 1/1977 Gristina
5,336,267 A 8/1994 Kubein-meesenburg et al.
(Continued)

FOREIGN PATENT DOCUMENTS

CN 108697509 A 10/2018
EP 0850609 A1 7/1998
(Continued)

OTHER PUBLICATIONS

"U.S. Appl. No. 15/293,373, Examiner Interview Summary dated Dec. 21, 2018", 4 pgs.
(Continued)

*Primary Examiner* — Brian A Dukert
(74) *Attorney, Agent, or Firm* — Schwegman Lundberg & Woessner, P.A.

(57) ABSTRACT

The present disclosure relates to a shoulder prosthesis comprising a glenoidal component having a glenoidal articulation surface and a humeral component having a humeral articulation surface, and a separate mobile glenohumeral bearing component comprising a glenoidal bearing surface and a humeral bearing surface arranged on opposite sides of the glenohumeral bearing component. The glenoidal bearing surface contacts in an implanted state the glenoidal articulation surface and/or the humeral bearing surface contacts in an implanted state the humeral articulation surface. At least one of the glenoidal and humeral bearing surfaces is concave. The glenohumeral bearing component is disposed in an implanted state between the glenoidal component and the humeral component. Both the glenoidal and humeral articulation surfaces are convex.

15 Claims, 5 Drawing Sheets

Figure 1:
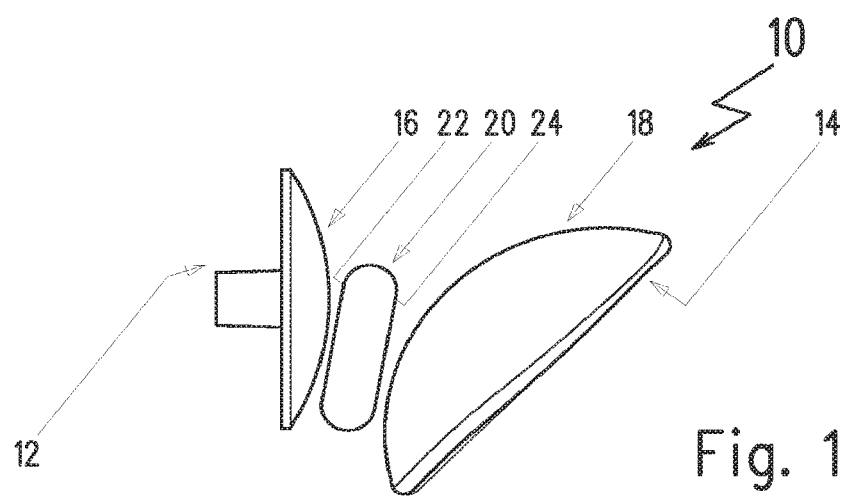

(52) U.S. Cl.
CPC . *A61F 2002/302* (2013.01); *A61F 2002/4018* (2013.01); *A61F 2002/4085* (2013.01)

(56) References Cited

U.S. PATENT DOCUMENTS

| | | | |
|---|---|---|---|
| 5,593,445 | A | 1/1997 | Waits |
| 5,723,018 | A | 3/1998 | Cyprien et al. |
| 7,033,396 | B2 * | 4/2006 | Tornier ................. A61F 2/32 623/19.11 |
| 7,241,314 | B1 | 7/2007 | Winslow |
| 7,799,077 | B2 | 9/2010 | Lang et al. |
| 8,425,614 | B2 | 4/2013 | Winslow et al. |
| 9,408,652 | B2 | 8/2016 | Hassler et al. |
| 9,763,797 | B2 | 9/2017 | Hopkins et al. |
| 2004/0220673 | A1 | 11/2004 | Pria |
| 2006/0009852 | A1 | 1/2006 | Winslow et al. |
| 2007/0225818 | A1 | 9/2007 | Reubelt et al. |
| 2009/0112328 | A1 * | 4/2009 | Tornier ................. A61F 2/40 623/18.11 |
| 2009/0287309 | A1 | 11/2009 | Walch et al. |
| 2011/0098822 | A1 | 4/2011 | Walch et al. |
| 2011/0118846 | A1 | 5/2011 | Katrana et al. |
| 2011/0264153 | A1 | 10/2011 | Hassler et al. |
| 2013/0053969 | A1 | 2/2013 | Linares et al. |
| 2015/0289985 | A1 | 10/2015 | Hopkins |
| 2017/0105843 | A1 | 4/2017 | Britton et al. |

FOREIGN PATENT DOCUMENTS

| | | | |
|---|---|---|---|
| EP | 1393697 B1 | 2/2006 | |
| EP | 1649836 A2 * | 4/2006 | ............... A61F 2/40 |
| EP | 1649836 A2 | 4/2006 | |
| EP | 1598034 B1 | 3/2011 | |
| EP | 2382930 A1 | 11/2011 | |
| EP | 2749255 A1 | 7/2014 | |
| JP | H06189987 | 7/1994 | |
| JP | 2007202965 | 8/2007 | |
| JP | 2018530397 A | 10/2018 | |
| WO | WO-9410941 | 5/1994 | |
| WO | WO-2007057054 A1 | 5/2007 | |
| WO | WO-2012125704 A2 | 9/2012 | |
| WO | WO-2014102141 A1 | 7/2014 | |
| WO | WO-2017066504 A1 | 4/2017 | |

OTHER PUBLICATIONS

"U.S. Appl. No. 15/293,373, Final Office Action dated Oct. 26, 2018", 19 pgs.

"U.S. Appl. No. 15/293,373, Response filed Dec. 26, 2018 to Final Office Action dated Oct. 26, 2018", 17 pgs.

"Australian Application Serial No. 2016339995, First Examination Report dated Jul. 20, 2018", 3 pgs.

"Australian Application Serial No. 2016339995, Subsequent Examiners Report dated Sep. 12, 2018", 4 pgs.

"U.S. Appl. No. 15/293,373, Non Final Office Action dated Aug. 21, 2017", 21 pgs.

"U.S. Appl. No. 14/439,605, Final Office Action dated Oct. 12, 2016", 12 pgs.

"U.S. Appl. No. 14/439,605, Non Final Office Action dated Mar. 16, 2016", 11 pgs.

"U.S. Appl. No. 14/439,605, Notice of Allowance dated Feb. 2, 2017", 5 pgs.

"U.S. Appl. No. 14/439,605, Notice of Allowance dated May 25, 2017", 5 pgs.

"U.S. Appl. No. 14/439,605, Preliminary Amendment filed Apr. 29, 2015", 9 pgs.

"U.S. Appl. No. 14/439,605, Response filed Jan. 12, 2017 to Final Office Action dated Oct. 12, 2016", 16 pgs.

"U.S. Appl. No. 14/439,605, Response filed Aug. 5, 2016 to Non Final Office Action dated Mar. 16, 2016", 13 pgs.

"International Application Serial No. PCT/EP2013/077419, International Preliminary Report on Patentability dated Jun. 30, 2015", 9 pgs.

"International Application Serial No. PCT/EP2013/077419, International Search Report dated Jan. 30, 2014", 5 pgs.

"International Application Serial No. PCT/US2016/056935, International Search Report dated Jan. 18, 2017", 6 pgs.

"International Application Serial No. PCT/US2016/056935, Written Opinion dated Jan. 18, 2017", 7 pgs.

"U.S. Appl. No. 15/293,373, Final Office Action dated Mar. 14, 2018", 20 pgs.

"U.S. Appl. No. 15/293,373, Response filed Jun. 14, 2018 to Final Office Action dated Mar. 14, 2018", 19 pgs.

"U.S. Appl. No. 15/293,373, Response Filed Dec. 20, 2017 to Non-Final Office Action dated Aug. 21, 2017", 13 pgs.

"International Application Serial No. PCT/US2016/056935, International Preliminary Report on Patentability dated Apr. 26, 2018", 9 pgs.

"U.S. Appl. No. 15/293,373, Advisory Action dated Jan. 14, 2019", 3 pgs.

"U.S. Appl. No. 15/293,373, Examiner Interview Summary dated Jan. 18, 2019", 3 pgs.

"European Application Serial No. 16787980.8, Response filed Jan. 7, 2019 to Office Action dated Jul. 26, 2018", 13 pgs.

"Japanese Application Serial No. 2018-519286, Notification of Reasons for Rejection dated Mar. 26, 2019", w English Translation, 11 pgs.

"U.S. Appl. No. 15/293,373, Appeal Brief Under 37 CFR § 41.37 Filed Mar. 29, 2019", 29 pgs.

"U.S. Appl. No. 15/293,373, Examiner Interview Summary dated Jul. 17, 2019", 3 pgs.

"U.S. Appl. No. 15/293,373, Non Final Office Action dated Jun. 13, 2019", 19 pgs.

"Canadian Application Serial No. 3,001,838, Examiner's Rule 30(2) Requisition dated Aug. 8, 2019", 5 pgs.

"Japanese Application Serial No. 2018-519286, Response filed Jun. 19, 2019 to Notification of Reasons for Rejection dated Mar. 26, 2019", w/English Translation, 10 pgs.

"U.S. Appl. No. 15/293,373, Response Filed Sep. 12, 2019 to Non-Final Office Action dated Jun. 13, 2019", 18 pgs.

"Chinese Application Serial No. 201680069210.3, Office Action dated Aug. 14, 2019", w/ English translation, 6 pgs.

"Chinese Application Serial No. 201680069210.3, Response filed Nov. 15, 2019 to Office Action dated Aug. 14, 2019", w/ English claims, 9 pgs.

"U.S. Appl. No. 15/293,373, Final Office Action dated Jan. 21, 2020", 22 pages.

"Canadian Application Serial No. 3,001,838, Response filed Feb. 4, 2020 to Examiner's Rule 30(2) Requisition dated Aug. 8, 2019", 3 pages.

"Chinese Application Serial No. 201680069210.3, Office Action dated Mar. 30, 2020", with English translation, 5 pages.

"Chinese Application Serial No. 201680069210.3, Response filed Apr. 23, 2020 to Office Action dated Mar. 30, 2020", with English claims, 25 pages.

"U.S. Appl. No. 15/293,373, Response filed Apr. 21, 2020 to Final Office Action dated Jan. 21, 2020", 12 pages.

"U.S. Appl. No. 15/293,373, Examiner Interview Summary dated Apr. 21, 2020", 3 pages.

* cited by examiner

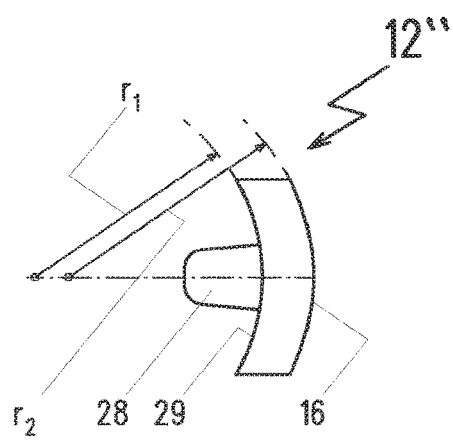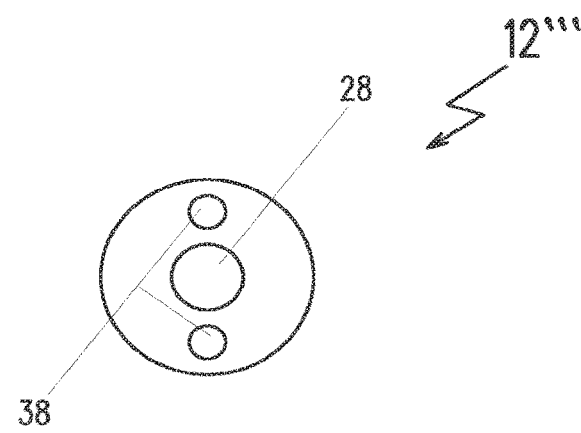
Fig. 11a   Fig. 11b
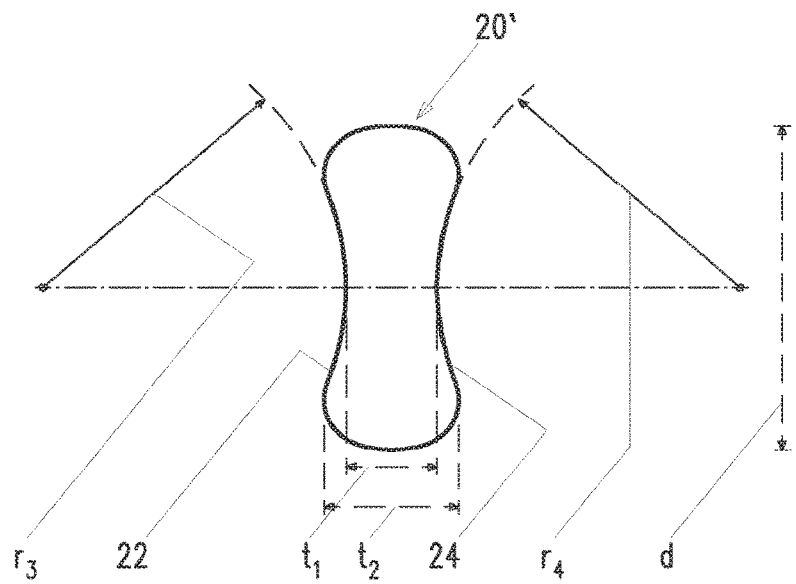
Fig. 12
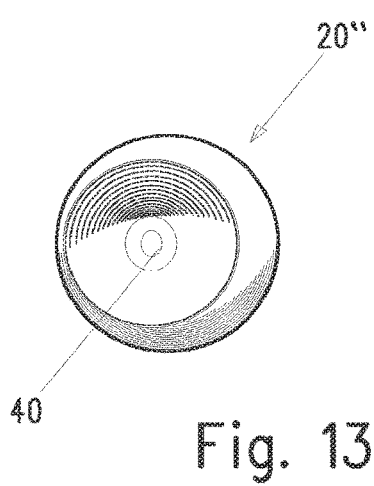 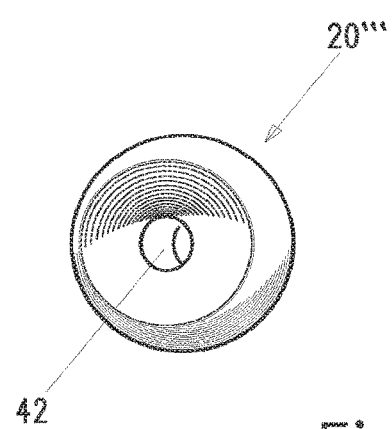
Fig. 13   Fig. 14

SHOULDER PROSTHESIS AND COMPONENTS THEREOF

The present disclosures relates to a shoulder prosthesis to be used in shoulder arthroplasty.

Shoulder pathology often involves disruption of the glenohumeral joint and/or an impairment of its functional components. A suitable treatment can involve a prosthetic replacement of the affected components of the natural joint. A partial reconstruction of the glenohumeral joint comprises the replacement of the natural articulation surface of the glenoidal component or the humeral component of the shoulder. In a complete reconstruction of the glenohumeral joint—also referred to as total shoulder arthroplasty (TSA)—both of the natural components mentioned above are replaced by prosthetic implants.

Documents EP 0 850 609 A1, US 2009/0112328 A1, U.S. Pat. No. 7,799,077 B2 and U.S. Pat. No. 5,593,445 A disclose exemplary shoulder joint prostheses with kinematics mimicking in principle the kinematics of a natural shoulder joint, i.e. the humeral component of the prostheses is provided with a convex articulation surface. Document EP 1 649 836 A2 discloses a prosthesis with an inverse kinematics. A further exemplary shoulder joint prosthesis is disclosed by WO 94/10941 A1.

Here, a novel concept of a shoulder prosthesis is suggested that has improved kinematics and that can be reliably fixed to the bone components involved.

The shoulder prosthesis according to claim 1 is provided with a glenoidal component having a glenoidal articulation surface and a humeral component having a humeral articulation surface. In other words, it is possible to provide a shoulder prosthesis comprising only a glenoidal component or a humeral component. Further, a separate mobile glenohumeral bearing component comprising a glenoidal bearing surface and a humeral bearing surface arranged on opposite sides of the glenohumeral bearing component is provided. The glenoidal bearing surface contacts in an implanted state the glenoidal articulation surface. Alternatively or additionally, the humeral bearing surface contacts in an implanted state the humeral articulation surface. At least one of the glenoidal and humeral bearing surfaces is concave.

Such a design has the advantages of a mobile bearing that acts as interpositional spacer while being very compact and having advantageous kinematic properties. The concave shape of at least one of the bearing surfaces brings the articulation close to the center of the prosthesis leading to an articulation kinematics that resembles closely the natural articulation. Further, a reduction of the stress and strain exerted on the components of the prostheses and adjacent portions the humerus and/or the scapula can be achieved.

"Mobile" in the context of the present disclosure should be understood as not being mounted to any bone or any other prosthetic component. Hence, the glenohumeral bearing component is merely in articulation contact with the glenoidal component and/or humeral component and is not provided with bone attachment means that secure the glenohumeral bearing component to one or both of said components. The glenohumeral bearing component is thus allowed to move—constrained only by the shape of the interacting surfaces—in reaction to a relative displacement and/or relative rotation of these components. The glenohumeral bearing component can therefore assume automatically an optimal position that reduces contact stresses acting between the functional elements involved.

The glenoidal articulation surface is convex. Hence, the glenoidal articulation surface of the glenoidal component is inverted compared to the natural osseous anatomy shifting the focus of the articulation towards the humeral head.

In yet another embodiment of the shoulder prosthesis, the glenoidal and humeral bearing surfaces have different curvatures and/or sizes to obtain the desired articulation kinematics of the prosthesis. In particular, the glenoidal bearing surface is smaller than the glenoidal articulation surface and/or the humeral bearing surface is smaller than the humeral articulation surface. However, in one embodiment the curvatures and/or the sizes of said surfaces are similar or identical. It is thus possible to choose said parameters as needed to realize the desired articulation kinematics.

According to another embodiment of the shoulder prosthesis according to the present disclosure, the glenohumeral bearing component comprises a central recess in the glenoidal bearing surface and/or the humeral bearing surface. Alternatively, a central opening extending from the glenoidal bearing surface to the humeral bearing surface may be provided. In other words, the glenohumeral bearing component may be provided with a recess and/or a hole in or close to the center of the bearing component in order to reduce the weight of the bearing component without comprising its functionality.

The shoulder prosthesis comprises both the glenoidal component and the humeral component, wherein the glenohumeral bearing component is disposed in an implanted state between the glenoidal component and the humeral component. Thus, the glenoidal component and the humeral component are not in direct contact and the glenohumeral bearing component acts as interpositional-spacer between the prosthetic articulation surfaces of said components. Both the glenoidal and humeral articulation surfaces are convex to concentrate the kinematic center of the prosthesis on the glenohumeral bearing component. In such an embodiment, both the bearing surfaces of the glenohumeral bearing component are concave, so that the spatial separation of the articulation surfaces—natural or prosthetic—is rather small in an implanted state of the prosthesis. This concept is in particular suited in cases where a total shoulder arthroplasty is indicated.

In another embodiment of the shoulder prosthesis, the glenoidal component comprises a glenoidal bone interface provided to be attached to the scapula of a patient and/or the humeral component comprises a humeral bone interface provided to be attached to a humerus of the patient, wherein the glenoidal bone interface or the humeral bone interface of the respective implant component is concave. In particular, both the glenoidal and humeral bone interfaces of the respective implant component are concave. Providing the glenoidal bone interface and/or the humeral bone interface with a concave design reduces tensile stress acting between the bone interface and the bone, especially when eccentric loads are applied. A concave geometry realigns the loads towards the center thereby reducing the occurrence of tensile stress that are particularly detrimental to the fixation reliability at the margin of the respective prosthetic component. In other words, the load distribution acting on the subchondral bone underlying the prosthetic component is improved by providing said component with a concave bone interface. Further, the surgical impact associated with implanting a shoulder prosthesis with a concave glenoidal bone interface and/or a concave humeral bone interface is reduced since less bone material has to be resected. Moreover, as bone material is preserved the convex bone surface adapted to receive such a concave bone interface can—if necessary— be converted by resection relatively easily into a planar or concave surface in case the respective prosthetic component has to be replaced. It should be noted that the advantageous effects associated with a concave bone interface can in principle also be realised in shoulder prosthesis which are not provided with a mobile bearing component and/or which are provided with a bearing component without at least one concave bearing surface.

The glenoidal bone interface may be disposed on a glenoidal base element that couples with an articulation element of the glenoidal component carrying the glenoidal articulation surface via a first coupling means and/or the humeral bone interface may be disposed on a humeral base element that couples with an articulation element of the prosthetic humeral component carrying the humeral articulation surface via a second coupling means. Said first and/or second coupling means may comprise at least one screw, a taper and/or snap means. In other words, the glenoidal component and/or the humeral component may comprise at least two separate elements provided with different functionalities. For example, first the corresponding base element is fixed to the bone and the articulation element is attached to the base element after it has been made sure that the base element is reliably fixed to the bone. Such an approach may facilitate the implantation of the shoulder prosthesis.

According to an embodiment of the shoulder prosthesis, the glenohumeral bearing component is made of ceramic and/or polyethylene. The glenoidal component—if applicable the glenoidal articulation element and/or the glenoidal base element—and/or the humeral component—if applicable the humeral articulation element and/or the humeral base element—may be made of metal, metal alloy, ceramic and/or polyethylene.

To be able to mimic the natural articulation of a shoulder joint and/or to provide the patient with a shoulder prosthesis adapted to his specific needs, the respective curvatures of the articulation surfaces and of the bearing surfaces have to be adjusted accordingly. However, it is not imperative that the articulation surfaces have identical curvatures or that the bearing surfaces have identical curvatures. It is also not imperative to provide the bearing surfaces with the same curvature as the corresponding articulation surfaces. In particular, the curvature of the glenoidal articulation surface and the curvature of the humeral articulation surface may be different from each other and different from that of the corresponding bearing surface. Specifically, the curvature of a concave surface may be smaller than that of the corresponding convex surface with which it is in contact.

Apart from the curvature of the cooperating surfaces, the thickness and the diameter of the glenohumeral component play an important role in determining the kinematics of the shoulder prosthesis. Hence, these parameters may also be chosen freely to achieve the desired kinematics.

Another important aspect influencing the kinematics of the shoulder prosthesis is the friction between the components of the shoulder prosthesis during articulation. In an embodiment of the shoulder prosthesis according to the present disclosure, the glenoidal articulation surface, the humeral articulation surface, the glenoidal bearing surface and the humeral bearing surface are designed such and/or the materials of said components are chosen such that a first coefficient of friction between the glenoidal articulation surface and the glenoidal bearing surface and a second coefficient or friction between the humeral articulation surface and humeral bearing surface are essentially equivalent. However, different coefficients of friction may be envisaged to create specific kinematic situations in order to meet the individual needs of a given patient. Different coefficients of friction may focus the kinematics and/or the associated loads on the humeral side or the glenoidal side of the shoulder prosthesis.

Further, a prosthetic glenoidal component of a shoulder prosthesis is suggested that reduces tensile loads acting between said component and the bone to which it is fixed.

Said prosthetic glenoidal component comprises a glenoidal articulation surface adapted to cooperate directly or indirectly via a glenohumeral bearing component with a natural or with a prosthetic humeral articulation surface. Said prosthetic glenoidal component further comprises a glenoidal bone interface provided to be attached to the scapula of a patient, wherein the glenoidal bone interface is concave. The advantages associated with a concave bone interface have been described in detail above in connection with a shoulder prosthesis according to the present disclosure. These considerations apply analogously to the prosthetic glenoidal component according to the present disclosure.

According to an embodiment of the prosthetic glenoidal component, the glenoidal articulation surface is convex.

Further, a glenohumeral bearing component is suggested that is adapted to be used in a shoulder prosthesis according to any of the embodiments described above.

In an embodiment of the glenohumeral bearing component, the glenohumeral bearing component comprises a glenoidal bearing surface and a humeral bearing surface arranged on opposite sides of the glenohumeral bearing component. One of the glenoidal bearing and the humeral bearing surfaces is concave and the other of the glenoidal bearing and the humeral bearing surfaces is one of planar, convex or concave.

A method for implanting a shoulder prosthesis is suggested, comprising the steps of providing a prosthetic glenoidal component comprising a glenoidal articulation surface and/or providing a prosthetic humeral component comprising a humeral articulation surface, resecting a glenoidal portion of a patient's scapula and attaching the glenoidal component to the resected glenoidal portion and/or resecting a proximal end of a patient's humerus and attaching the humeral component to the resected proximal end portion, and inserting a glenohumeral bearing component comprising a glenoidal bearing surface and a humeral bearing surface, wherein the glenoidal bearing surface contacts in an implanted state the glenoidal articulation surface and/or wherein the humeral bearing surface contacts in an implanted state the humeral articulation surface. At least one of the glenoidal and humeral bearing surfaces is concave.

According to an embodiment of the method, the step of resecting the glenoidal portion of a patient's scapula comprises the step of preparing a convex bone portion adapted to match a correspondingly shaped—in particular concave—bone interface of the glenoidal component.

In another embodiment of the method, the step of providing a glenoidal component comprises providing a glenoidal component comprising a convex glenoidal articulation surface.

In yet another embodiment of the method, the step of attaching the glenoidal component to the resected glenoidal portion comprises placing the glenoidal component on the convex bone portion and fixing it to the scapula using at least one of a screw, bone cement and a press fit means.

A further method of implanting a shoulder prosthesis comprises the steps of providing a prosthetic glenoidal component comprising a glenoidal articulation surface and a glenoidal bone interface provided to be attached to a scapula of a patient, resecting a glenoidal portion of a patient's scapula to form a convex bone portion adapted to match the correspondingly shaped—in particular concave—glenoidal bone interface and fixing the glenoidal component to the resected glenoidal portion.

The different embodiments of the shoulder prosthesis, the prosthetic glenoidal component, the glenohumeral bearing component and the methods of implanting a shoulder prosthesis described above in accordance with the scope of the independent claims and the features realized there can naturally be combined with one another.

Further embodiments of the disclosure are also recited in the dependent claims, the description and the drawings.

Further areas of applicability of the present disclosure will become apparent from the detailed description provided hereinafter. It should be understood that the detailed description and the specific examples are intended for purpose of illustration only and are not intended to limit the scope of the invention in any way. The figures are simplified in schematic. Details not necessary for the understanding of the invention are omitted.

Figure 2:
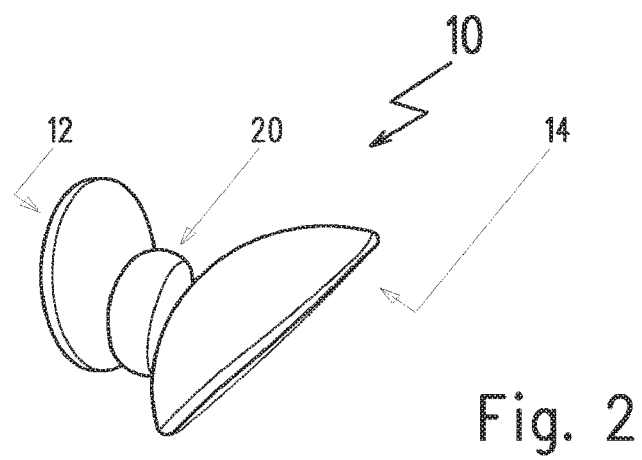
Figure 3:
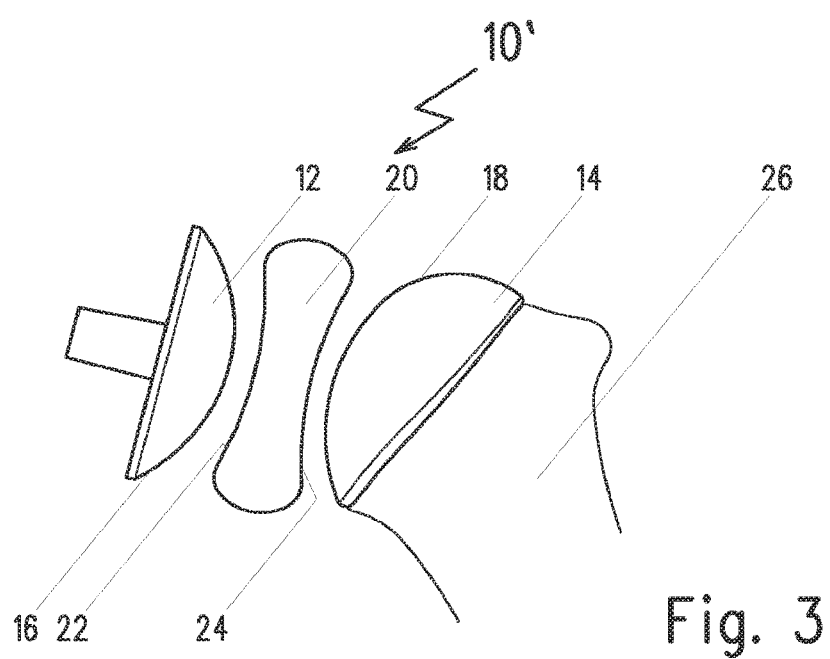
Figure 4:
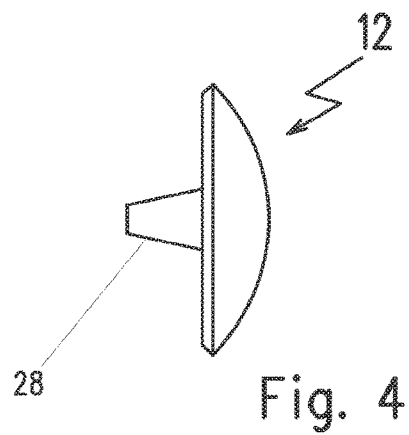
Figure 5:
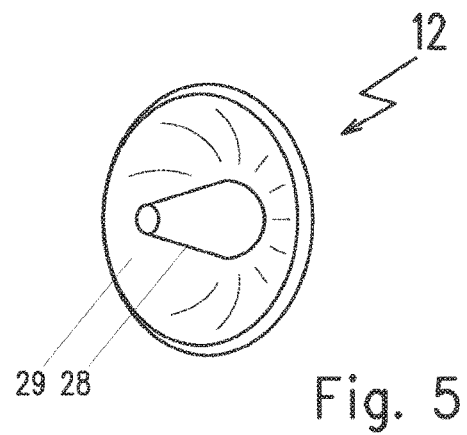
Figure 6:
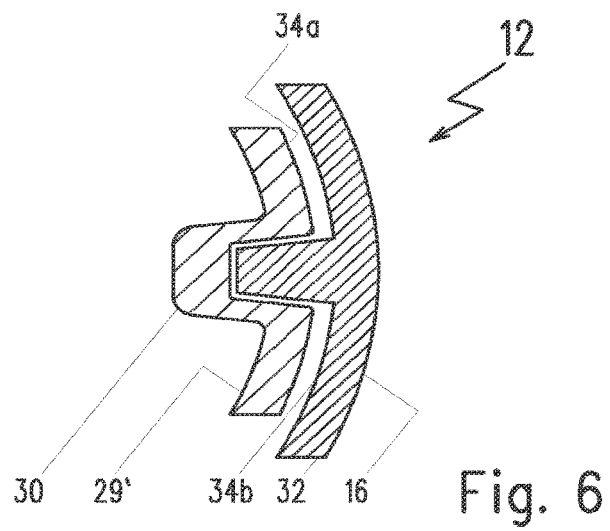
Figure 7A:
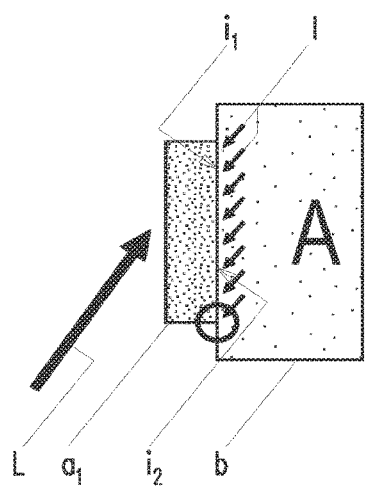
Figure 7B:
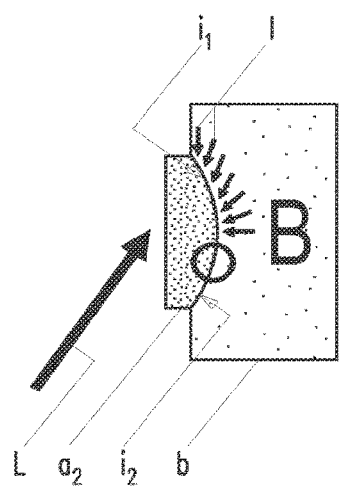
Figure 7C:
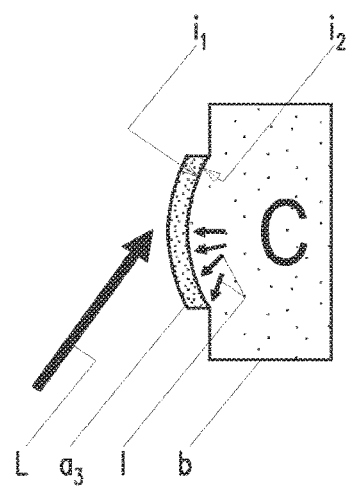
Figure 8A:
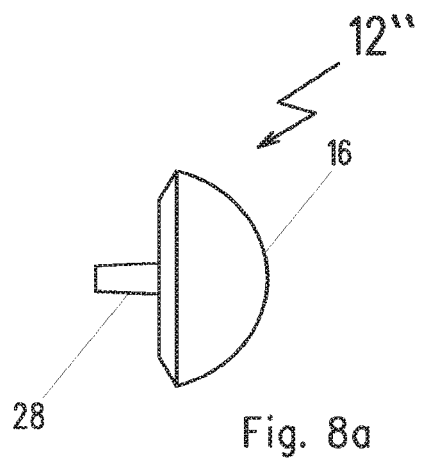
Figure 8B:
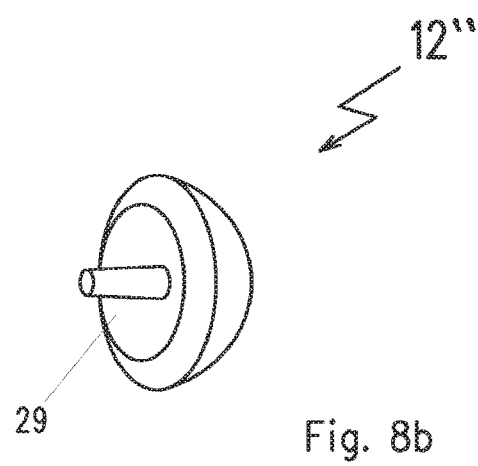
Figure 9:
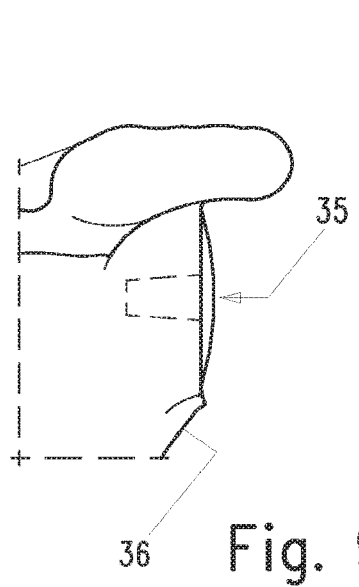
Figure 10:
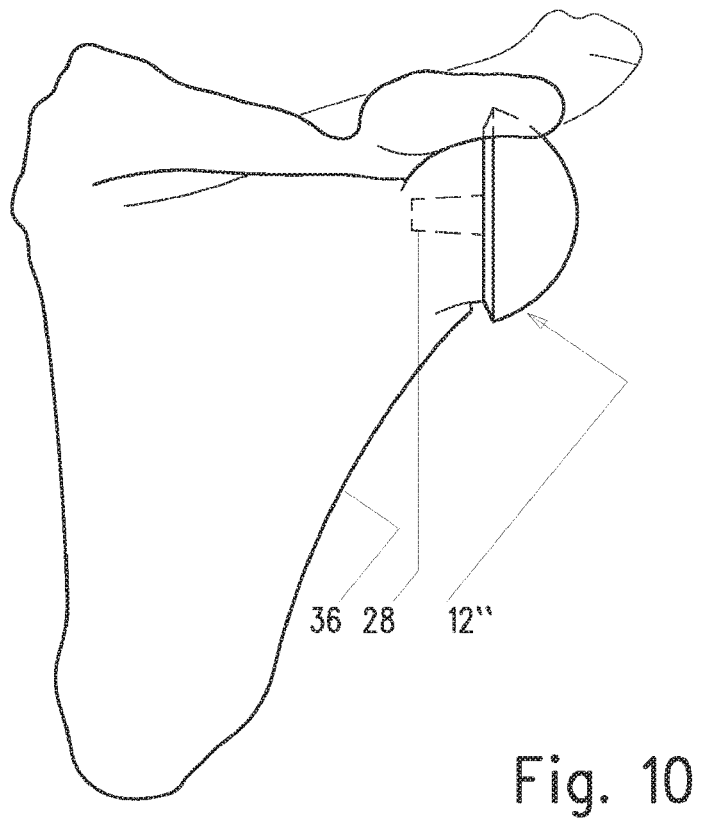
Figure 15:
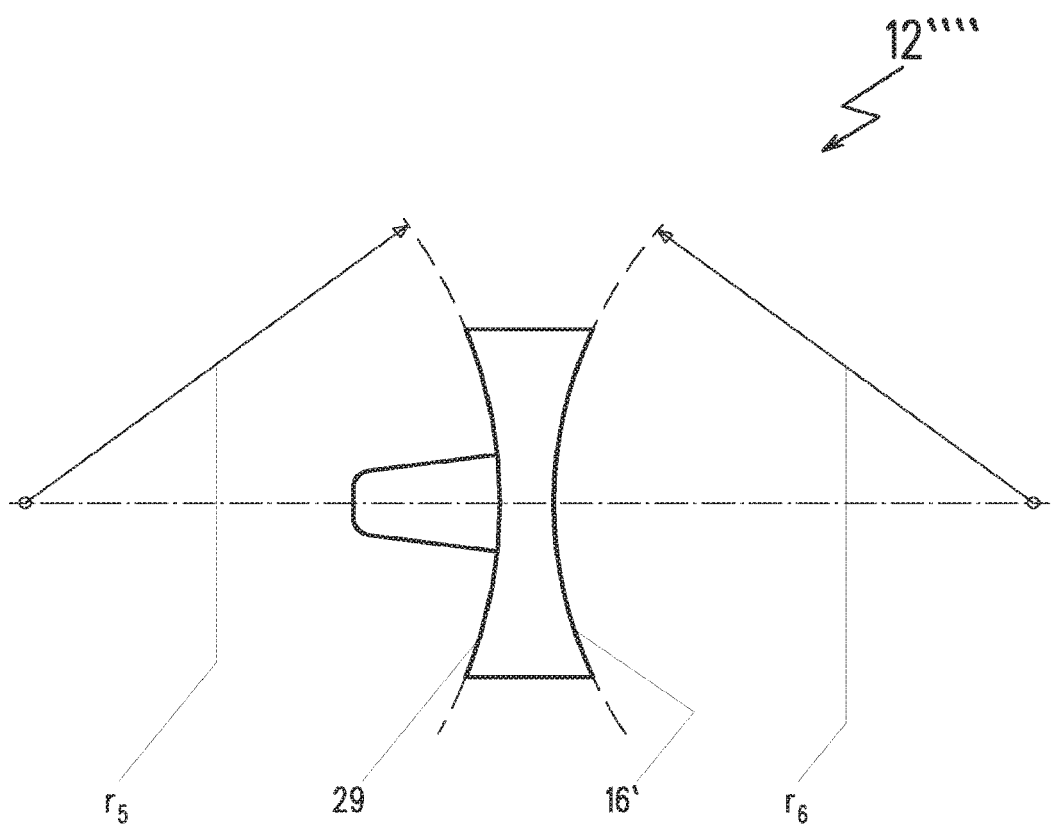
Figure 16:
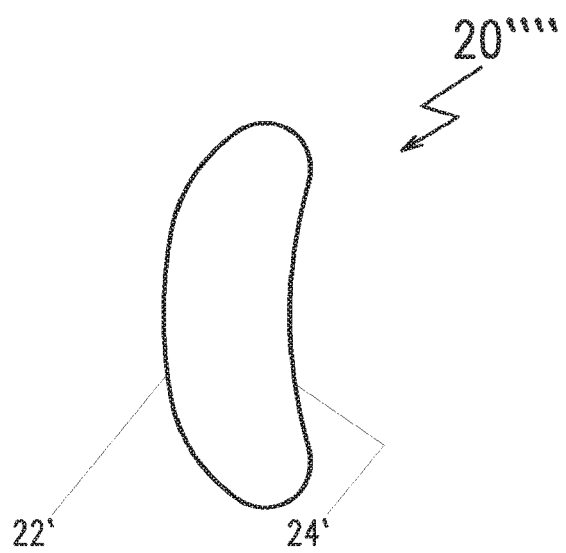

The present disclosure will be explained in more detail and become fully understood from the detailed description and the accompanying drawings, wherein FIGS. 1 and 2 depict an embodiment of the shoulder prosthesis in accordance with the present disclosure in different perspective views, FIG. 3 shows schematically a similar embodiment of the shoulder prosthesis in accordance with the present disclosure, FIGS. 4 and 5 show schematically an embodiment of the prosthetic glenoidal component in accordance with the present disclosure, FIG. 6 shows an embodiment of the prosthetic glenoidal component comprising a base element and an articulation element, FIGS. 7a to 7c show load distributions resulting from different bone interface geometries, FIGS. 8a and 8b show yet another embodiment of the prosthetic glenoidal component in accordance with the present disclosure in different views, FIG. 9 shows a scapula resected to receive the glenoidal component of FIGS. 9a and 9b, FIG. 10 shows the glenoidal component of FIGS. 9a and 9b attached to the resected scapula, FIGS. 11a and 11b show a further embodiment of the prosthetic glenoidal component in accordance with the present disclosure, FIGS. 12 to 14 show different embodiments of a glenohumeral bearing component in accordance with the present disclosure, FIG. 15 shows an embodiment of a prosthetic glenoidal component in accordance with the present disclosure and FIG. 16 shows yet another embodiment of a glenohumeral bearing component in accordance with the present disclosure.

FIG. 1 shows a shoulder prosthesis 10 comprising a glenoidal component 12 attached in an implanted state to a scapula of a patient and a humeral component 14 attached in an implanted state to a humeral head of the humerus of a patient. Glenoidal component 12 comprises—contrary to the natural anatomy—a convex glenoidal articulation surface 16. Humeral component 14 is provided with a humeral articulation surface 18.

In an implanted state, surfaces 16, 18 are not in direct contact with each other but are separated by glenohumeral bearing component 20. Glenohumeral bearing component 20 therefore acts as a spacer disposed between components 12, 14. Glenohumeral bearing component 20 comprises a glenoidal bearing surface 22 that is in an implanted state of prosthesis 10 in contact with glenoidal articulation surface 16. On the opposite side, glenohumeral bearing component 20 is provided with humeral bearing surface 24 that is in an implanted state of prosthesis 10 in contact with humeral articulation surface 18.

Glenohumeral bearing component 20 is not attached to neither of components 12, 14. It can therefore move freely relative to surfaces 16, 18. The movement of glenohumeral bearing component 20 relative to components 12, 14 is in essence governed by the geometry and properties of surfaces 16, 18, 22, 24 and the loads applied to the prosthesis during articulation of the shoulder. In other words, glenohumeral bearing component 20 is a separate, mobile component and shoulder prosthesis 10 can be described as a mobile bearing shoulder system particularly suitable for total shoulder arthroplasty intended for patients who have intact and functional rotor cuff musculature. However, it should be understood, that the principle of the shoulder prosthesis according to the present disclosure can also be applied to prostheses used in partial shoulder arthroplasty in which e.g. the natural humeral head is preserved.

FIG. 2 shows shoulder prosthesis 10 in an perspective view to display the lens-like design of glenohumeral bearing component 20. In this example, the glenohumeral bearing component 20 has the shape of a concave-concave lens. However, it should be appreciated that convex-concave or concave-convex designs are also conceivable.

FIG. 3 shows schematically a shoulder prosthesis 10' which is functionally similar to shoulder prosthesis 10. Humeral component 14 of shoulder prosthesis 10' is fixed to the proximal end of humerus 26 replacing—at least partially—its head. The natural articulation surface of humerus 26 has therefore been substituted by prosthetic articulation surface 18 of humeral component 14.

It can be seen from FIG. 3 that both bearing surfaces 22, 24 of glenohumeral bearing component 20 are concave and that no attachment means are provided to secure or fix component 20 to one of or both components 12, 14. A movement of glenohumeral bearing component 20 relative to components 12, 14 during articulation of the shoulder is constrained by the geometry of surfaces 16, 18, 22, 24, the loads applied and the friction between surfaces 16, 22 on the one hand and the friction between surfaces 18, 24 on the other hand. Due to the concave design of surfaces 22, 24, the kinematics of shoulder prosthesis 10'- and similarly the kinematics of prosthesis 10—concentrates close to the center of glenohumeral bearing component 20. In contrast, if surfaces 22, 24 would be both convex, the motion of glenoidal component 12 relative to glenohumeral component 20 on one the hand and the motion of humeral component 14 relative to glenohumeral bearing component 20 one the other hand would be spatially separated substantially leading to an unnatural overall articulation kinematics. Hence, shoulder prosthesis 10' combines the advantages of a mobile bearing system with a compact design without compromising a natural articulation.

In other words, the mobile bearing concept of the present disclosure comprises a glenohumeral bearing component 20 that is compact—in most cases smaller than components 12, 14—and that is free to articulate and to move between components 12, 14. The geometry of surfaces 16, 18, 22, 24 and the loads applied during articulation create forces that automatically shift glenohumeral bearing component 20 in the optimal position which leads to a reduction of contact stresses.

Moreover, the concave design of surfaces 22, 24 allows providing a mobile bearing prosthesis with a minimized distance between components 12, 14 which in turn reduces the surgical impact of the implantation of a shoulder prosthesis according to the present disclosure.

FIG. 4 shows glenoidal component 12 of prosthesis 10' in a sideview. Glenoidal component 12 can be attached to the scapula of a patient via tapered peg 28. In principle, all known concepts of attaching a prosthesis to a bone can be contemplated when choosing a suitable approach to fix component 12 to the scapula. The same applies to means and methods for fixing humeral component 14 to humerus 26.

FIG. 5 shows schematically glenoidal component 12 from the bone interface side to visualize the geometry of a bone interface surface 29 of glenoidal component 12. It is not flat but has a concave shape from which peg 28 extends.

As depicted in FIG. 6, instead of a direct fixation of glenoidal component 12 to the scapula, it may be envisaged to provide a glenoidal component 12' with a base element 30 comprising a concave bone interface surface 29'. Base element 30 receives an articulation element 32 comprising glenoidal articulation surface 16. Glenoidal component 12' therefore comprises two separate elements 30, 32 with different functionalities. Base element 30 and articulation element 32 of glenoidal component 12' comprise convex and concave contacting surfaces 34a, 34b, respectively, which are in contact in an assembled state of glenoidal component 12'.

Exemplarily, first base element 30 is attached to the bone during implantation of component 12'. Then, articulation element 32 is attached to base element 30 in a following step. Thus, base element 30 serves as an anchor that allows to fix articulation element 32 to the bone. It should be understood that humeral component 14 may be designed analogously.

FIGS. 7a to 7c show the effect of the geometry of the bone interface surface on the stress and strain regime during articulation in a generalized form.

In all shown cases the load acting on a prosthetic component or implant $a_1$, $a_2$, $a_3$ attached to a bone b is depicted by arrow L. The resultant stress produced in bone b is indicated by small arrows 1.

In FIG. 8a, both a bone interface surface $i_1$ of implant $a_1$ and resected bone surface $i_2$ of bone b receiving bone interface surface $i_1$ are essentially flat. This geometry leads to tensile forces especially in the areas denoted by a circle.

In FIG. 8b, implant $a_2$ is provided with a convex bone interface surface $i_1$ cooperating with a concave resected bone surface $i_2$. Load L generates compressional reaction forces on the upper end of implant $a_1$. In the lower part parasitic tensile forces are generated, again indicated exemplarily by a circle.

In FIG. 8c implant $a_3$ has a concave bone interface surface $i_1$ cooperating with a convex resected bone surface $i_2$. Load L is realigned by this geometry towards a central region of implant $a_3$ thereby greatly reducing the occurrence of tensile forces that are especially detrimental for the fixation of an implant to a bone.

FIGS. 8a and 8b show a further embodiment 12" of a glenoidal component with a concave bone interface surface 29. It can be seen that glenoidal component 12" is more massive than glenoidal components 12, 12' and that the curvature of its articulation surface 16 is larger.

FIG. 9 shows a portion of a patient's scapula 36 prepared to receive glenoidal component 12". A suitably resected bone surface 35 is convex. The preparation involves only a minor bone resection conserving enough natural bone material for later revisions of the shoulder prosthesis, if needed.

FIG. 10 shows glenoidal component 12" fixed to scapula 36. It should be understood that the fixation of glenoidal component 12" may involve more than one fixation pegs or other suitable fixation means instead of or in addition to peg 28. Bone cement can be used to assist the fixation of glenoidal component 12" to scapula 36.

FIG. 11a shows a further embodiment 12'" of a glenoidal component provided with a relatively massive fixation peg 28—optimized for a press fit—extending from bone interface surface 29. It can be seen that a curvature radius $r_1$ of bone interface surface 29 is smaller than a curvature radius $r_2$ of glenoidal articulation surface 16. The center of radius $r_2$ is shifted towards component 12'" to compensate the fact that surfaces 29, 16 are spaced apart.

FIG. 11b depicts a backview of glenoidal component 12'" revealing that it is provided—in addition to centrally arranged peg 28—with screw holes 38 that can be used to improve the fixation of glenoidal component 12'" to the bone, if needed. Of course, only one screw hole 38 or more that two screw holes 38 can be provided.

FIG. 12 shows an lens-like embodiment 20' of a glenohumeral bearing component according to the present disclosure. Both the glenoidal bearing surface 22 and the humeral bearing surface 24 are defined by a specific curvature suitably chosen in consideration of the curvature of the corresponding articulation surface 16, 18, respectively. Specifically, glenoidal bearing surface 22 has a curvature radius $r_3$ and humeral bearing surface 24 has a curvature radius $r_4$. Curvature radii $r_3$, $r_4$ can be chosen as needed, e.g. $r_3=r_4$, $r_3>r_4$, $r_3<r_4$. Further parameters that might be chosen freely in order to obtain the desired kinematics are—inter alia—a diameter d of glenohumeral bearing component 20' or its minimum thickness $t_1$ and/or its maximum thickness $t_2$.

FIGS. 13 and 14 show further embodiments 20", 20'", respectively, of a glenohumeral bearing component according to the present disclosure. Glenohumeral bearing component 20" shown in FIG. 13 is provided with a recess 40 in the center of surfaces 22, 24, so that the contact with articulation surfaces 16, 18, respectively, concentrates in a ring-like region around recess 40.

As it can be seen in FIG. 14, instead of recesses 40, a hole 42 can be provided in a central region of glenohumeral bearing component 20'" in order to save even more material and to reduce its weight. Figuratively speaking, glenohumeral bearing component 20'" is toroidally shaped, i.e. resembles a doughnut. The removal of material in a central region of glenohumeral bearing components 20", 20'" does not compromise the kinematics of the shoulder prosthesis when combined with suitable glenoidal and humeral components.

FIG. 15 discloses a further embodiment 12"" of a glenoidal component according to the present disclosure. Glenoidal component 12"" has a concave bone interface surface 29 with a curvature radius $r_5$ and a concave glenoidal articulation surface 16' with a curvature radius $r_6$. Radii $r_5$, $r_6$ may be equal or different.

Exemplarily, a glenoidal component 12"" as depicted in FIG. 15 may be used in combination with a humeral component 14 as shown e.g. in FIGS. 1 to 3. A suitable glenohumeral bearing component 20"" is shown in FIG. 16. It has a convex glenoidal bearing surface 22' and a concave humeral bearing surface 24'. Hence, glenohumeral bearing component 20"" has a more bean-like appearance compared to the lens-like shape of glenohumeral bearing components 20, 20', 20", 20'".

It should be understood that glenohumeral bearing component 20"" can also be used in shoulder prostheses with a convex glenoidal articulation surface and a concave humeral articulation surface.

LIST OF REFERENCE NUMBERS 10, 10' shoulder prosthesis
12, 12', 12", 12'", 12"" glenoidal component
14 humeral component
16, 16' glenoidal articulation surface
18 humeral articulation surface
20, 20', 20", 20'", 20"" glenohumeral bearing component
22, 22' glenoidal bearing surface
24, 24' humeral bearing surface
26 humerus
28 peg
29, 29' bone interface surface
30 base element
32 articulation element
34a, 34b contacting surface
35 resected bone surface
36 scapula
38 screw hole
40 recess
42 hole
$r_1, r_2, r_3, r_4, r_5, r_6$ curvature radius
$a_1, a_2, a_3$ implant
L, l load
b bone
$i_1$ bone interface surface
$i_2$ resected bone surface
$t_1, t_2$ thickness
d diameter

The invention claimed is:

1. A shoulder prosthesis comprising:
a glenoidal component including a glenoidal articulation surface;
a humeral component including a humeral articulation surface; and
a mobile glenohumeral bearing component including an exterior glenoidal bearing surface and an exterior humeral bearing surface arranged on opposite sides of the glenohumeral bearing component, wherein the glenoidal and humeral bearing surfaces are both concave, and wherein the glenohumeral bearing component is disposed, in an implanted state, between the glenoidal component and the humeral component such that the glenoidal bearing surface contacts the glenoidal articulation surface and the humeral bearing surface contacts the humeral articulation surface.

2. The shoulder prosthesis of claim 1, wherein the glenohumeral bearing component is lens-shaped.

3. The shoulder prosthesis of claim 1, the glenoidal component comprising a base element adapted to be secured to a scapula and an articulation element adapted to be secured to the base element, the articulation element including the glenoidal articulation surface.

4. The shoulder prosthesis of claim 1, the humeral component comprising a base element adapted to be secured to a humerus and an articulation element adapted to be secured to the base element, the articulation element including the humeral articulation surface.

5. The shoulder prosthesis of claim 1, wherein the glenoidal component includes a concave bone interface surface adapted to engage a convex resected surface of a scapula.

6. The shoulder prosthesis of claim 1, wherein the glenohumeral bearing component includes an opening extending from the glenoidal bearing surface to the humeral bearing surface.

7. The shoulder prosthesis of claim 1, wherein the glenoidal and humeral bearing surfaces comprise different curvatures.

8. A shoulder prosthesis comprising:
a glenoidal component including a glenoidal articulation surface;
a humeral component including a humeral articulation surface, wherein both the glenoidal and humeral articulation surfaces are convex; and
a mobile glenohumeral bearing component including an exterior glenoidal bearing surface and an exterior humeral bearing surface arranged on opposite sides of the glenohumeral bearing component, wherein the glenohumeral bearing component is disposed, in an implanted state, between the glenoidal component and the humeral component such that the glenoidal bearing surface contacts the glenoidal articulation surface and the humeral bearing surface contacts the humeral articulation surface.

9. The shoulder prosthesis of claim 8, wherein at least one of the glenoidal and humeral bearing surfaces is concave.

10. The shoulder prosthesis of claim 8, wherein the glenoidal and humeral bearing surfaces comprise different curvatures.

11. The shoulder prosthesis of claim 8, wherein when the glenohumeral bearing component is in the implanted state, the glenohumeral bearing component is mobile relative to at least one of the glenoidal component and the humeral component.

12. A shoulder prosthesis comprising:
a glenoidal component including a glenoidal articulation surface defining a glenoidal articulation curvature;
a humeral component including a humeral articulation surface defining a humeral articulation curvature, wherein at least one of the glenoidal and humeral articulation surfaces is convex; and
a mobile glenohumeral bearing component including an exterior glenoidal bearing surface and an exterior humeral bearing surface arranged on opposite sides of the glenohumeral bearing component, the glenoidal bearing surface defining a glenoidal bearing curvature and the humeral bearing surface defining a humeral bearing curvature that is different from the glenoidal bearing curvature such that a bearing thickness defined between the glenoidal and humeral bearing surfaces varies along the glenohumeral bearing component, wherein when the glenohumeral bearing component is in an implanted state, the glenohumeral bearing component is mobile relative to the glenoidal component and the humeral component, due to the absence of physical attachment between the glenohumeral bearing component and the glenoidal and humeral components, thereby enabling the glenohumeral bearing component to move freely and articulate relative to the glenoidal articulation surface and the humeral articulation surface;
wherein the glenoidal articulation curvature is different from the glenoidal bearing curvature, the humeral articulation curvature is different from the humeral bearing curvature, or both the glenoidal and humeral articulation curvatures are different from the corresponding glenoidal and humeral bearing curvatures.

13. The shoulder prosthesis of claim 12, wherein at least one of the glenoidal and humeral bearing surfaces is concave.

14. The shoulder prosthesis of claim 13, wherein the glenoidal and humeral bearing surfaces are both concave.

15. The shoulder prosthesis of claim 12, wherein the glenohumeral bearing component is lens-shaped.

\* \* \* \* \*